US010165368B2

(12) United States Patent
Kulavik et al.

(10) Patent No.: US 10,165,368 B2
(45) **Date of Patent: *Dec. 25, 2018**

(54) METHOD AND SYSTEM FOR HEADSET WITH AUTOMATIC SOURCE DETECTION AND VOLUME CONTROL

(71) Applicant: Voyetra Turtle Beach, Inc., Valhalla, NY (US)

(72) Inventors: Richard Kulavik, San Jose, CA (US); Shobha Devi Kuruba Buchannagari, San Jose, CA (US)

(73) Assignee: Voyetra Turtle Beach, Inc., Valhalla, NY (US)

(*) Notice: Subject to any disclaimer, the term of this patent is extended or adjusted under 35 U.S.C. 154(b) by 41 days.

This patent is subject to a terminal disclaimer.

(21) Appl. No.: 14/855,737

(22) Filed: Sep. 16, 2015

(65) Prior Publication Data

US 2016/0192074 A1 Jun. 30, 2016

Related U.S. Application Data

(63) Continuation of application No. 14/508,367, filed on Oct. 7, 2014, now Pat. No. 9,143,878.

(Continued)

(51) Int. Cl.
*H04R 5/02* (2006.01)
*H04R 5/04* (2006.01)

(Continued)

(52) U.S. Cl.
CPC ............... *H04R 5/04* (2013.01); *H04R 5/033* (2013.01); *H04S 1/005* (2013.01); *H04S 3/004* (2013.01);

(Continued)

(58) Field of Classification Search
CPC ........ H04S 1/00; H04S 1/005; H04S 2400/01; H04S 3/004; H04S 7/00; H04S 7/40;

(Continued)

(56) References Cited

U.S. PATENT DOCUMENTS 6,614,912 B1 * 9/2003 Yamada .................. H04S 1/005 381/310
6,961,632 B2 * 11/2005 Hashimoto ............. H04S 1/002 700/94

(Continued)

OTHER PUBLICATIONS

PCT International Search Report dated Jan. 7, 2015 for PCT Patent Application No. PCT/US2014/59691.

(Continued)

*Primary Examiner* — Lun-See Lao
(74) *Attorney, Agent, or Firm* — McAndrews, Held & Malloy

(57) ABSTRACT

Methods and systems for headset with automatic source detection and volume control may include in an audio headset: receiving one or more audio signals carrying audio channels; and processing the audio channels to generate stereo signals for output to a left and a right speaker of the audio headset. The processing may include: determining a quantity of the audio channels carried in the received audio signals by comparing a level of a channel of the received audio signals to a threshold during a determined time period; adjusting a level of one or more of the audio channels based on the quantity of the audio channels carried in the received audio signals; and combining the audio channels to generate the stereo signals. The processing may include adjusting gain and/or phase of the audio channels carried in the received audio signals such that a perceived location of a listener is changed.

20 Claims, 11 Drawing Sheets

Related U.S. Application Data

(60) Provisional application No. 61/888,666, filed on Oct. 9, 2013.

(51) Int. Cl.
*H04S 1/00* (2006.01)
*H04S 3/00* (2006.01)
*H04R 5/033* (2006.01)

(52) U.S. Cl.
CPC .... *H04R 2205/021* (2013.01); *H04R 2430/01* (2013.01); *H04S 2400/01* (2013.01)

(58) Field of Classification Search
CPC .. G10K 11/16; G10K 11/178; G10K 11/1784; G10K 2210/00; G10K 2210/108; G10K 2210/3014; G10K 2210/3017; G10K 2210/3028; G10K 2210/30391; G10L 19/008
USPC ......... 381/74, 77, 56, 370, 17–23, 104–107, 381/120, 1, 300, 119; 379/430; 700/94; 455/3, 6
See application file for complete search history.

(56) References Cited

U.S. PATENT DOCUMENTS

| | | | | |
|---|---|---|---|---|
| 8,265,293 | B2 * | 9/2012 | Park | H04B 1/034 381/57 |
| 8,788,077 | B2 * | 7/2014 | Goldstein | A61B 5/6817 381/56 |
| 9,143,878 | B2 * | 9/2015 | Kulavik | H04S 1/005 |
| 2002/0038158 | A1 * | 3/2002 | Hashimoto | H04S 1/002 700/94 |
| 2004/0136538 | A1 | 7/2004 | Cohen et al. | |
| 2005/0117761 | A1 | 6/2005 | Sato | |
| 2007/0160218 | A1 * | 7/2007 | Jakka | H04S 3/004 381/22 |
| 2008/0318518 | A1 * | 12/2008 | Coutinho | H04H 20/62 455/3.06 |
| 2009/0232317 | A1 * | 9/2009 | Emerit | H04S 3/008 381/17 |
| 2010/0040240 | A1 | 2/2010 | Bonanno | |

OTHER PUBLICATIONS

PCT International Preliminary Report dated Apr. 21, 2016 for PCT Patent Application No. PCT/US2014/59691.
Extended European Search Report dated May 15, 2017 for European Patent Application No. 14852043.0.

* cited by examiner

METHOD AND SYSTEM FOR HEADSET WITH AUTOMATIC SOURCE DETECTION AND VOLUME CONTROL

PRIORITY CLAIM

This patent application is a continuation of U.S. patent application Ser. No. 14/508,367 (now U.S. Pat. No. 9,143,878) filed on Oct. 7, 2014, which in turn, claims priority to U.S. Provisional Patent Application Ser. No. 61/888,666 filed on Oct. 9, 2013. Each of the above referenced documents is hereby incorporated herein by reference in its entirety.

TECHNICAL FIELD

Aspects of the present application relate to electronic gaming. More specifically, to methods and systems for headset with automatic source detection and volume control.

BACKGROUND

Limitations and disadvantages of conventional approaches to audio processing for gaming will become apparent to one of skill in the art, through comparison of such approaches with some aspects of the present method and system set forth in the remainder of this disclosure with reference to the drawings.

BRIEF SUMMARY

Methods and systems are provided for dynamic control of game audio based on audio analysis, substantially as illustrated by and/or described in connection with at least one of the figures, as set forth more completely in the claims.

DETAILED DESCRIPTION

Figure 1A:
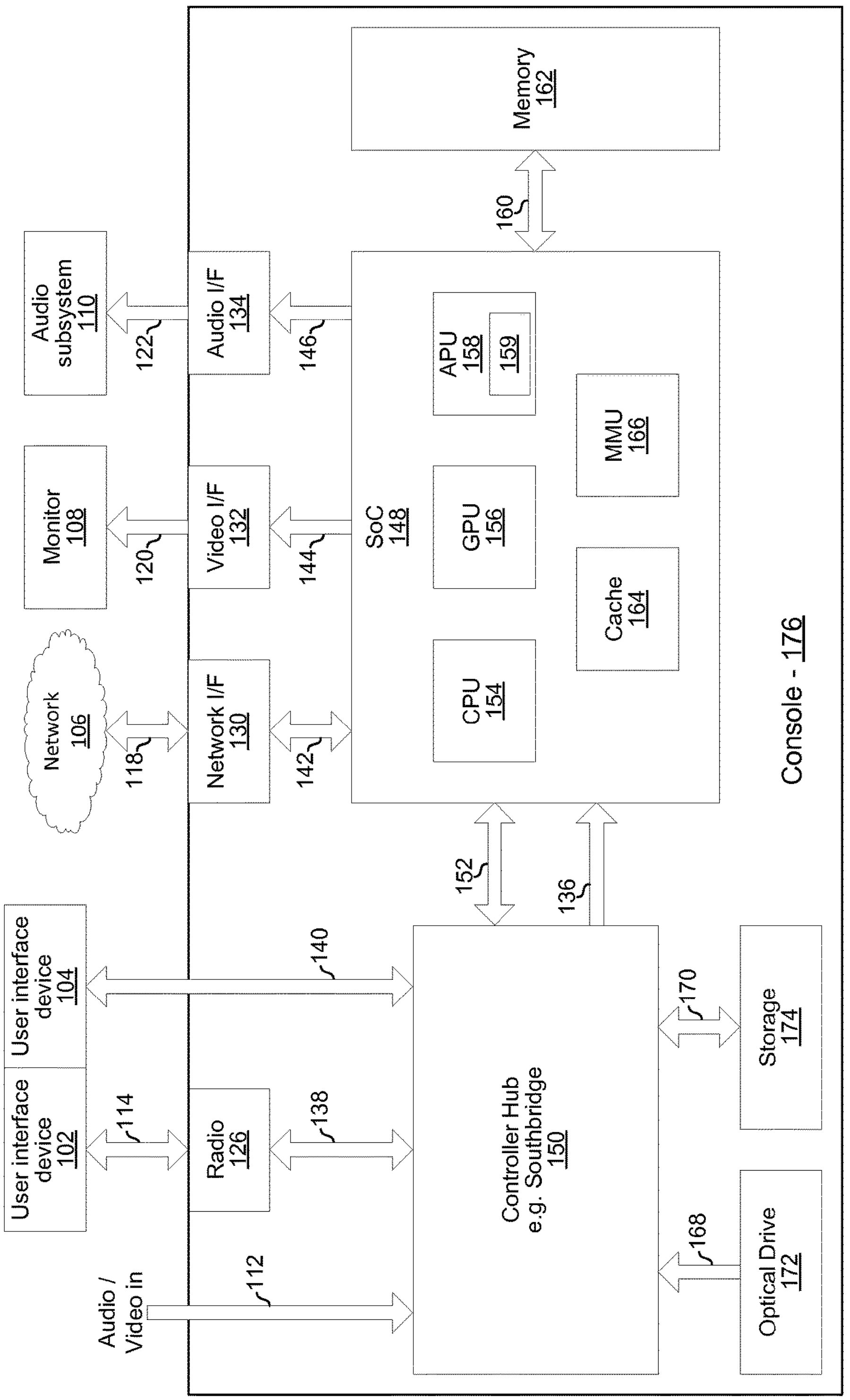
FIG. 1A is a diagram that depicts an example gaming console, which may be utilized to provide dynamic control of game audio based on audio analysis, in accordance with various exemplary embodiments of the disclosure.

FIG. 1A depicts an example gaming console, which may be utilized to provide dynamic control of game audio based on audio analysis, in accordance with various exemplary embodiment of the disclosure. Referring to FIG. 1A, there is shown a console 176, user interface devices 102, 104, a monitor 108, an audio subsystem 110, and a network 106.

The game console 176 may comprise suitable logic, circuitry, interfaces and/or code that may be operable to present a game to, and also enable game play interaction between, one or more local players and/or one or more remote players. The game console 176 which may be, for example, a Windows computing device, a Unix computing device, a Linux computing device, an Apple OSX computing device, an Apple iOS computing device, an Android computing device, a Microsoft Xbox, a Sony Playstation, a Nintendo Wii, or the like. The example game console 176 comprises a radio 126, network interface 130, video interface 132, audio interface 134, controller hub 150, main system on chip (SoC) 148, memory 162, optical drive 172, and storage device 174. The SoC 148 comprises central processing unit (CPU) 154, graphics processing unit (GPU) 156, audio processing unit (APU) 158, cache memory 164, and memory management unit (MMU) 166. The various components of the game console 176 are communicatively coupled through various buses/links 136, 138, 142, 144, 146, 152, 160, 168, and 170.

The controller hub 150 comprises circuitry that supports one or more data bus protocols such as High-Definition Multimedia Interface (HDMI), Universal Serial Bus (USB), Serial Advanced Technology Attachment II, III or variants thereof (SATA II, SATA III), embedded multimedia card interface (e.MMC), Peripheral Component Interconnect Express (PCIe), or the like. The controller hub 150 may also be referred to as an input/output (I/O) controller hub. Exemplary controller hubs may comprise Southbridge, Haswell, Fusion and Sandybridge. The controller hub 150 may be operable to receive audio and/or video from an external source via link 112 (e.g., HDMI), from the optical drive (e.g., Blu-Ray) 172 via link 168 (e.g., SATA II, SATA III), and/or from storage 174 (e.g., hard drive, FLASH memory, or the like) via link 170 (e.g., SATA II, III and/or e.MMC). Digital audio and/or video is output to the SoC 148 via link 136 (e.g., CEA-861-E compliant video and IEC 61937 compliant audio). The controller hub 150 exchanges data with the radio 126 via link 138 (e.g., USB), with external devices via link 140 (e.g., USB), with the storage 174 via the link 170, and with the SoC 148 via the link 152 (e.g., PCIe).

The radio 126 may comprise suitable logic, circuitry, interfaces and/or code that may be operable to communicate in accordance with one or more wireless standards such as the IEEE 802.11 family of standards, the Bluetooth family of standards, near field communication (NFC), and/or the like.

The network interface 130 may comprise suitable logic, circuitry, interfaces and/or code that may be operable to communicate in accordance with one or more wired standards and to convert between wired standards. For example, the network interface 130 may communicate with the SoC 148 via link 142 using a first standard (e.g., PCIe) and may communicate with the network 106 using a second standard (e.g., gigabit Ethernet).

The video interface 132 may comprise suitable logic, circuitry, interfaces and/or code that may be operable to communicate video in accordance with one or more wired or wireless video transmission standards. For example, the video interface 132 may receive CEA-861-E compliant video data via link 144 and encapsulate/format, etc., the video data in accordance with an HDMI standard for output to the monitor 108 via an HDMI link 120.

The audio interface 134 may comprise suitable logic, circuitry, interfaces and/or code that may be operable to communicate audio in accordance with one or more wired or wireless audio transmission standards. For example, the audio interface 134 may receive CEA-861-E compliant audio data via the link 146 and encapsulate/format, etc. the video data in accordance with an HDMI standard for output to the audio subsystem 110 via an HDMI link 122.

The central processing unit (CPU) 154 may comprise suitable logic, circuitry, interfaces and/or code that may be operable to execute instructions for controlling/coordinating the overall operation of the game console 176. Such instructions may be part of an operating system of the console and/or part of one or more software applications running on the console.

The graphics processing unit (GPU) 156 may comprise suitable logic, circuitry, interfaces and/or code that may be operable to perform graphics processing functions such as compression, decompression, encoding, decoding, 3D rendering, and/or the like.

The audio processing unit (APU) 158 may comprise suitable logic, circuitry, interfaces and/or code that may be operable to perform audio processing functions such as volume/gain control, compression, decompression, encoding, decoding, surround-sound processing, and/or the like to output single channel or multi-channel (e.g., 2 channels for stereo or 6, 8, or more channels for surround sound) audio signals. The APU 158 comprises memory (e.g., volatile and/or non-volatile memory) 159 which stores parameter settings to affect processing of audio by the APU 158. For example, the parameter settings may include a first audio gain/volume setting that determines, at least in part, a volume of game audio output by the console 176 and a second audio gain/volume setting that determines, at least in part, a volume of chat audio output by the console 176. The parameter settings may be modified via a graphical user interface (GUI) of the console and/or via an application programming interface (API) provided by the console 176.

The cache memory 164 may comprise suitable logic, circuitry, interfaces and/or code that may provide high-speed memory functions for use by the CPU 154, GPU 156, and/or APU 158. The cache memory 164 may typically comprise DRAM or variants thereof. The memory 162 may comprise additional memory for use by the CPU 154, GPU 156, and/or APU 158. The memory 162, typically DRAM, may operate at a slower speed than the cache memory 164 but may also be less expensive than cache memory as well as operate at a higher speed than the memory of the storage device 174. The MMU 166 controls accesses by the CPU 154, GPU 156, and/or APU 158 to the memory 162, the cache 164, and/or the storage device 174.

In FIG. 1A, the example game console 176 is communicatively coupled to the user interface device 102, the user interface device 104, the network 106, the monitor 108, and the audio subsystem 110.

Each of the user interface devices 102 and 104 may comprise, for example, a game controller, a keyboard, a motion sensor/position tracker, or the like. The user interface device 102 communicates with the game console 176 wirelessly via link 114 (e.g., Wi-Fi Direct, Bluetooth, NFC and/or the like). The user interface device 102 may be operable to communicate with the game console 176 via the wired link 140 (e.g., USB or the like).

The network 106 comprises a local area network and/or a wide area network. The game console 176 communicates with the network 106 via wired link 118 (e.g., Gigabit Ethernet).

The monitor 108 may be, for example, a LCD, OLED, or PLASMA screen. The game console 176 sends video to the monitor 108 via link 120 (e.g., HDMI).

The audio subsystem 110 may be, for example, a headset, a combination of headset and audio basestation, or a set of speakers and accompanying audio processing circuit. The game console 176 sends audio to the audio subsystem 110 via link(s) 122 (e.g., S/PDIF for digital audio or "line out" for analog audio). Additional details of an example audio subsystem 110 are described below.

In accordance with an embodiment of the disclosure, the audio levels on the left channel and the right channel of a received signal may be monitored by a headset for a determined period of time in order to determine the type of input stream that is being received. During the monitoring of the audio levels on the audio channels, if the headset detects nothing, the headset may conclude that there is no audio. If audio is detected by the headset on only one channel and the detected audio level is above a first determined threshold, the headset may conclude that the audio is monophonic (mono). If audio is detected on both channels and the detected audio level on each channel is above a second determined threshold, the headset may conclude that the audio is at least stereo. If the audio is determined to be at least stereo, the headset may determine whether the audio is a surround sound format by checking whether the level(s) on the subwoofer channel and/or the center channel are above a third determined threshold. The subwoofer and/or center channel may be used for this determination because, in typical surround sound scenarios, there is almost always audio on the subwoofer channel, and, to a lesser extent, on the center channel, whereas the rear channels often have no audio for long periods of time. If the detected audio level on the subwoofer channel or the center channel is above the third determined threshold, the headset may conclude that at least 6 channels are present in the received signal. In instances where there is a need for the headset to distinguish between 6 channels (e.g., 5.1 Surround) from 8 channels (7.1 Surround), then the headset may determine whether the level(s) on one or both of the side channels is/are above a fourth determined threshold. If so, the headset may conclude that there are 8 channels. If detected audio levels on the side channels are not above that fourth threshold, then it may be concluded that there are 6 channels.

Once the headset determines the number of audio channels in the received audio, the headset may utilize resulting information to control the volume of the audio levels on one or more of the detected channels such that the resulting stereo output does not fluctuate beyond certain levels regardless of the number of audio channels in the received signal. In this regard, without such volume control based on the determined number of channels, the volume may need to be set to account for the highest overall volume that may result from combining the most possible number of channels. Such a setting, however, may often result in the overall volume being too low when there are a fewer number of channels actually present in the signal. Once the number of channels is known, the volume of the individual channels can be adjusted accordingly when combining them to form the output stereo signal. For example, if only a first and second channel are present in the received audio signal, a volume of each of the first and second channels may be set to the maximum volume limit permitted by applicable regulations, but if there is a third channel present that is to be combined with the first channel for output to the left speaker and combined with the second channel for output to the right speaker, then the volumes of the first and second channels may be set lower during the combining to account for the additional signal energy in the third channel such that the maximum overall volume output to each speaker can reach, but not exceed, the maximum volume limit permitted by applicable regulations Additionally, or alternatively, once the headset determines the number of audio channels in the received audio, the headset may utilize resulting information to process the input stream to create a desired surround effect (e.g., controlling the perceived location of the listener relative to the audio). Hysteresis of the audio channels may also be utilized as a factor by the headset to determine when to transition between the different types of input streams.

Figure 1B:
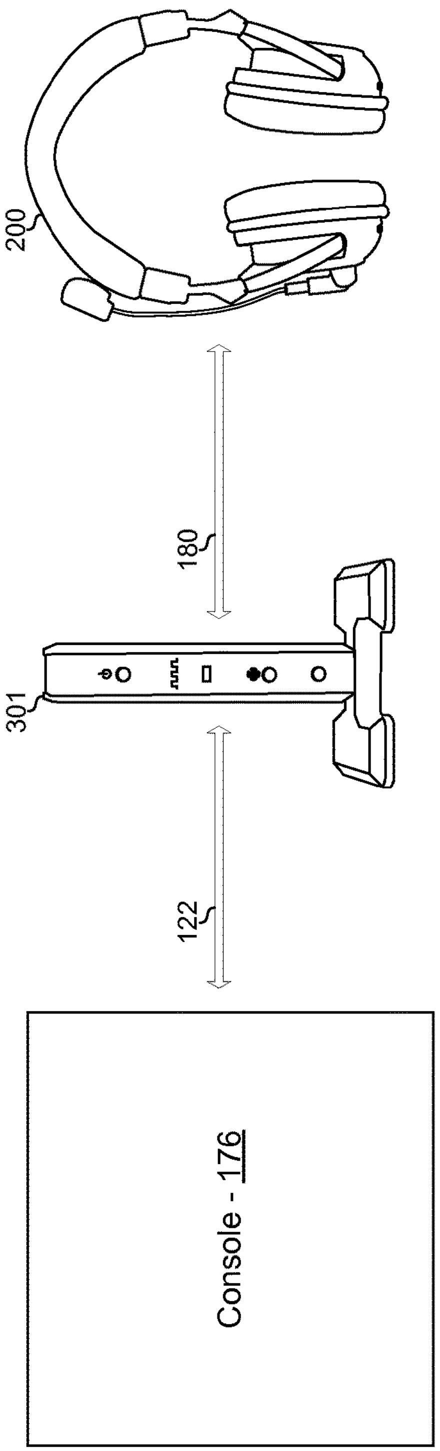
FIG. 1B is a diagram that depicts an example gaming audio subsystem comprising a headset and an audio basestation, in accordance with various exemplary embodiments of the disclosure.

FIG. 1B is a diagram that depicts an example gaming audio subsystem comprising a headset and an audio basestation, in accordance with various exemplary embodiments of the disclosure. Referring to FIG. 1B, there is shown a console 176, a headset 200 and an audio basestation 301. The headset 200 communicates with the basestation 301 via a link 180 and the basestation 301 communicates with the console 176 via a link 122. The link 122 may be as described above. In an example implementation, the link 180 may be a proprietary wireless link operating in an unlicensed frequency band. The headset 200 may be as described below with reference to FIGS. 2A-2C. The basestation 301 may be as described below with reference to FIGS. 3A-3B.

Figure 1C:
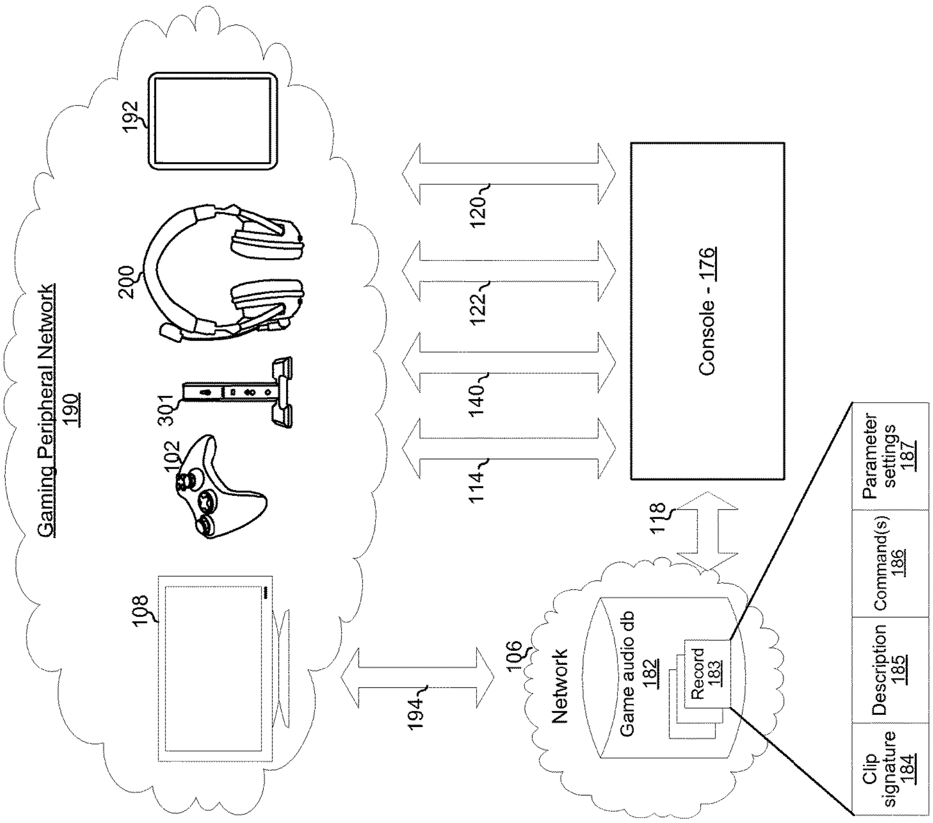
FIG. 1C is a diagram of an exemplary gaming console and an associated network of peripheral devices, in accordance with various exemplary embodiments of the disclosure.

FIG. 1C is a diagram of an exemplary gaming console and an associated network of peripheral devices, in accordance with various exemplary embodiments of the disclosure. Referring to FIG. 1C, there is shown is the console 176, which is communicatively coupled to a plurality of peripheral devices and a network 106. The example peripheral devices shown include a monitor 108, a user interface device 102, a headset 200, an audio basestation 301, and a multi-purpose device 192.

The monitor 108 and the user interface device 102 are as described above. The headset 200 is as described below with reference to FIGS. 2A-2C. The audio basestation is as described below with reference to, for example, FIGS. 3A-3B.

The multi-purpose device 192 may comprise, for example, a tablet computer, a smartphone, a laptop computer, or the like and that runs an operating system such as Android, Linux, Windows, iOS, OSX, or the like. An example multi-purpose device is described below with reference to FIG. 4. Hardware (e.g., a network adaptor) and software (i.e., the operating system and one or more applications loaded onto the device 192) may configure the device 192 for operating as part of the GPN 190. For example, an application running on the device 192 may cause display of a graphical user interface (GUI), which may enable a user to access gaming-related data, commands, functions, parameter settings, and so on. The graphical user interface may enable a user to interact with the console 176 and the other devices of the GPN 190 to enhance the user's gaming experience.

The peripheral devices 102, 108, 192, 200, 300 are in communication with one another via a plurality of wired and/or wireless links (represented visually by the placement of the devices in the cloud of GPN 190). Each of the peripheral devices in the gaming peripheral network (GPN) 190 may communicate with one or more others of the peripheral devices in the GPN 190 in a single-hop or multi-hop fashion. For example, the headset 200 may communicate with the basestation 301 in a single hop (e.g., over a proprietary RF link) and with the device 192 in a single hop (e.g., over a Bluetooth or Wi-Fi direct link), while the tablet may communicate with the basestation 301 in two hops via the headset 200. As another example, the user interface device 102 may communicate with the headset 200 in a single hop (e.g., over a Bluetooth or Wi-Fi direct link) and with the device 192 in a single hop (e.g., over a Bluetooth or Wi-Fi direct link), while the device 192 may communicate with the headset 200 in two hops via the user interface device 102. These example interconnections among the peripheral devices of the GPN 190 are merely examples, any number and/or types of links and/or hops among the devices of the GPN 190 is possible.

The GPN 190 may communicate with the console 176 via any one or more of the connections 114, 140, 122, and 120 described above. The GPN 190 may communicate with a network 106 via one or more links 194 each of which may be, for example, Wi-Fi, wired Ethernet, and/or the like.

A database 182 which stores gaming audio data is accessible via the network 106. The gaming audio data may comprise, for example, signatures of particular audio clips (e.g., individual sounds or collections or sequences of sounds) that are part of the game audio of particular games, of particular levels/scenarios of particular games, particular characters of particular games, etc. In an example implementation, the database 182 may comprise a plurality of records 183, where each record 183 comprises an audio clip (or signature of the clip) 184, a description of the clip 185 (e.g., the game it is from, when it occurs in the game, etc.), one or more gaming commands 186 associated with the clip, one or more parameter settings 187 associated with the clip, and/or other data associated with the audio clip. Records 183 of the database 182 may be downloadable to, or accessed in real-time by, one of more devices of the GPN 190.

Figure 2A:
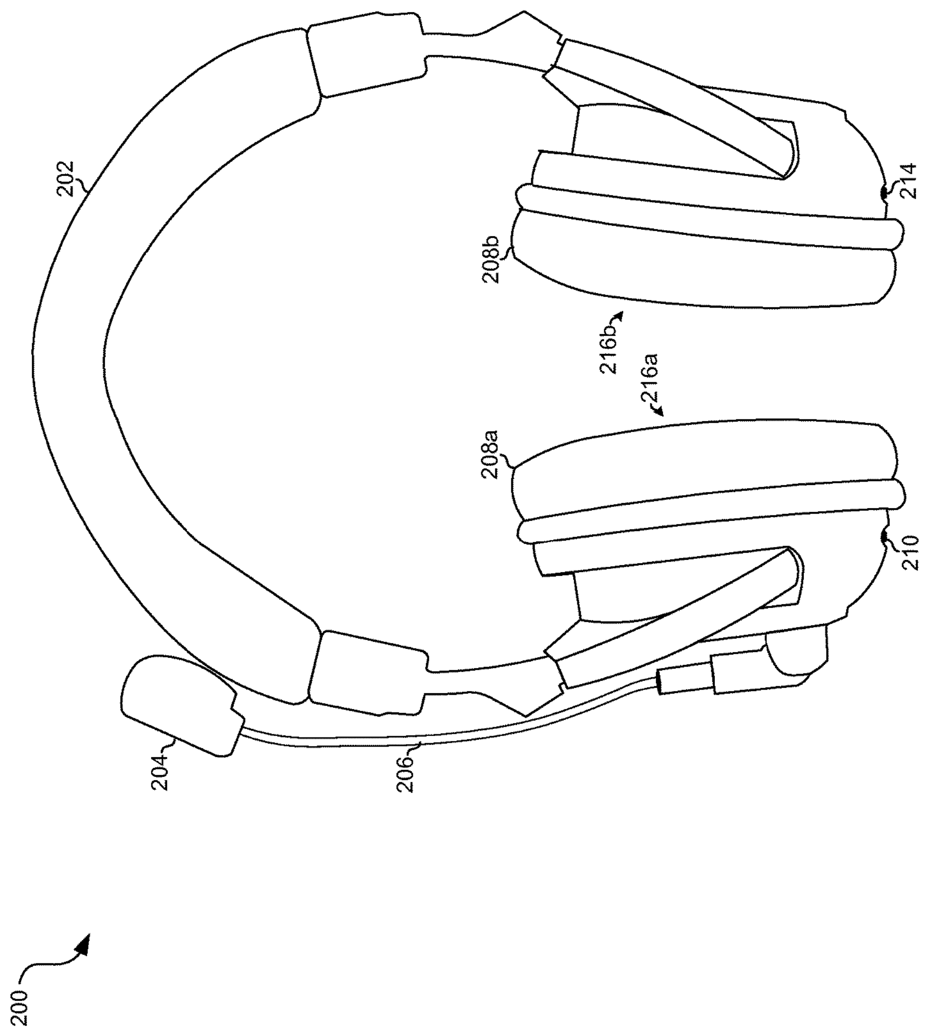
FIGS. 2A and 2B are diagrams that depict two views of an example embodiment of a gaming headset, in accordance with various exemplary embodiments of the disclosure.
Figure 2B:
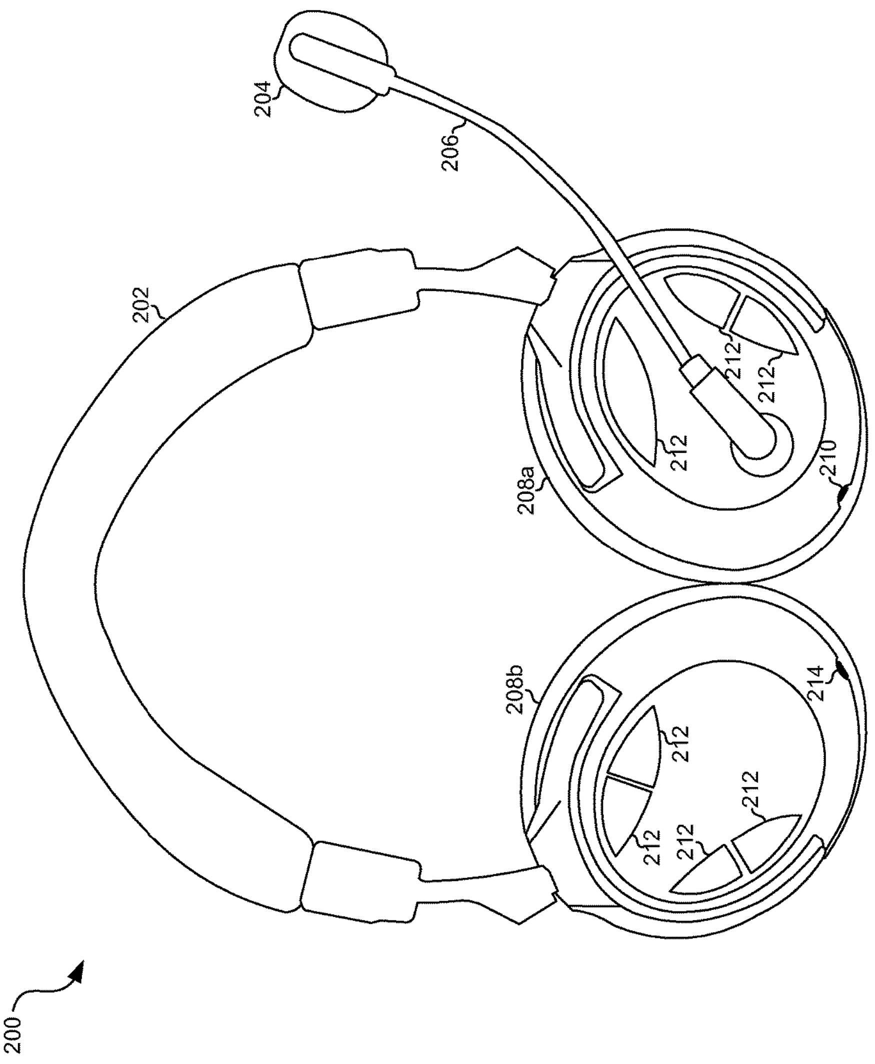

FIGS. 2A and 2B are diagrams that depict two views of an example embodiment of a gaming headset, in accordance with various exemplary embodiments of the disclosure. Referring to FIGS. 2A and 2B, there are shown two views of an example headset 200 that may present audio output by a gaming console such as the console 176. The headset 200 comprises a headband 202, a microphone boom 206 with microphone 204, ear cups 208*a* and 208*b* which surround speakers 216*a* and 216*b*, connector 210, connector 214, and user controls 212.

The connector 210 may be, for example, a 3.5 mm headphone socket for receiving analog audio signals (e.g., receiving chat audio via an Xbox "talkback" cable).

The microphone 204 may comprise suitable logic, circuitry, interfaces and/or code that may be operable to convert acoustic waves (e.g., the voice of the person wearing the headset) to electric signals for processing by circuitry of the headset and/or for output to a device (e.g., console 176, basestation 301, a smartphone, and/or the like) that is in communication with the headset.

The speakers 216*a* and 216*b* may comprise circuitry that may be operable to convert electrical signals to sound waves.

The user controls 212 may comprise dedicated and/or programmable buttons, switches, sliders, wheels, etc. for performing various functions. Example functions which the controls 212 may be configured to perform include: power the headset 200 on/off, mute/unmute the microphone 204, control gain/volume of, and/or effects applied to, chat audio by the audio processing circuit of the headset 200, control gain/volume of, and/or effects applied to, game audio by the audio processing circuit of the headset 200, enable/disable/initiate pairing (e.g., via Bluetooth, Wi-Fi direct, NFC, or the like) with another computing device, and/or the like. Some of the user controls 212 may adaptively and/or dynamically change during gameplay based on a particular game that is being played. Some of the user controls 212 may also adaptively and/or dynamically change during gameplay based on a particular player that is engage in the game play. The connector 214 may be, for example, a USB, thunderbolt, Firewire or other type of port or interface. The connector 214 may be used for downloading data to the headset 200 from another computing device and/or uploading data from the headset 200 to another computing device. Such data may include, for example, parameter settings (described below). Additionally, or alternatively, the connector 214 may be used for communicating with another computing device such as a smartphone, tablet compute, laptop computer, or the like.

Figure 2C:
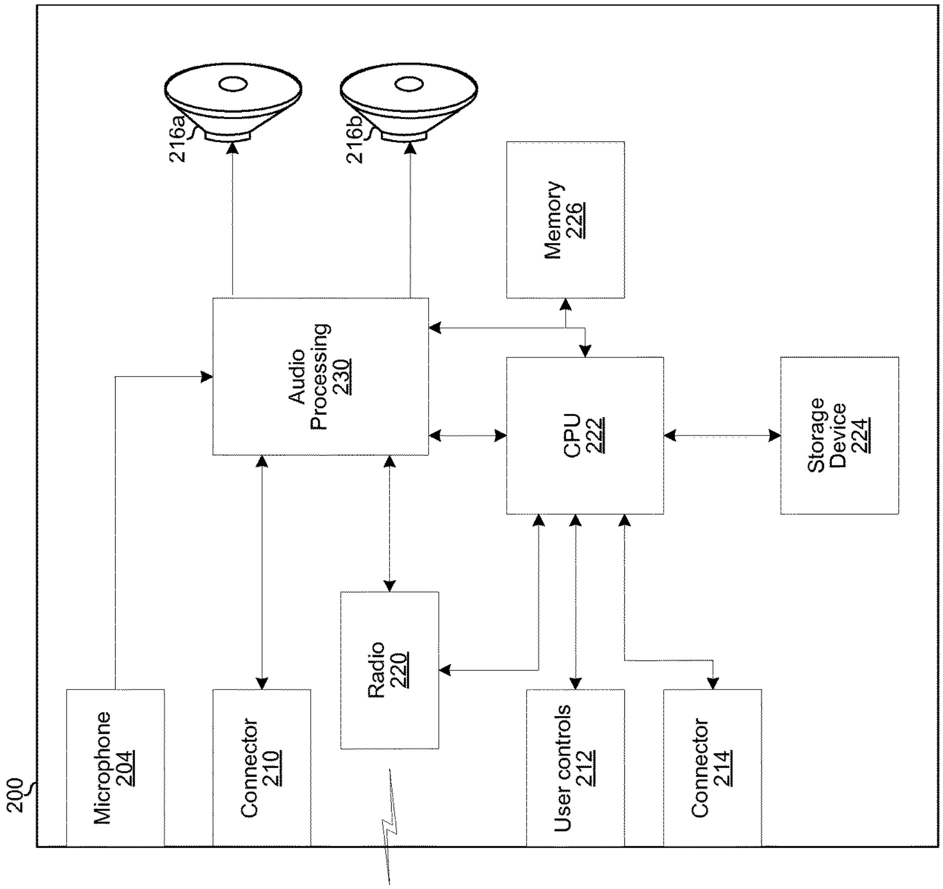
FIG. 2C is a diagram that depicts a block diagram of the example headset of FIGS. 2A and 2B, in accordance with various exemplary embodiments of the disclosure.

FIG. 2C is a diagram that depicts a block diagram of the example headset of FIGS. 2A and 2B, in accordance with various exemplary embodiments of the disclosure. Referring to FIG. 2C, there is shown a headset 200. In addition to the connector 210, user controls 212, connector 214, microphone 204, and speakers 216*a* and 216*b* already discussed, shown are a radio 220, a CPU 222, a storage device 224, a memory 226, and an audio processing circuit 230.

The radio 220 may comprise suitable logic, circuitry, interfaces and/or code that may be operable to communicate in accordance with one or more standardized (such as, for example, the IEEE 802.11 family of standards, NFC, the Bluetooth family of standards, and/or the like) and/or proprietary wireless protocol(s) (e.g., a proprietary protocol for receiving audio from an audio basestation such as the basestation 301).

The CPU 222 may comprise suitable logic, circuitry, interfaces and/or code that may be operable to execute instructions for controlling/coordinating the overall operation of the headset 200. Such instructions may be part of an operating system or state machine of the headset 200 and/or part of one or more software applications running on the headset 200. In some implementations, the CPU 222 may be, for example, a programmable interrupt controller, a state machine, or the like.

The CPU 222 may also be operable to handle dynamic control of game audio based on audio analysis of a received audio signal. In this regard, the CPU 222 may be operable to dynamically handle the increasing and decreasing (which may include muting/unmuting) of the level(s) of one or more audio channels detected in a received audio signal based on information determined from the audio analysis, which may be stored in the storage device 224 and/or the memory 226.

The storage device 224 may comprise suitable logic, circuitry, interfaces and/or code that may comprise, for example, FLASH or other nonvolatile memory, which may be operable to store data comprising operating data, configuration data, settings, and so on, which may be used by the CPU 222 and/or the audio processing circuit 230. Such data may include, for example, parameter settings that affect processing of audio signals in the headset 200 and parameter settings that affect functions performed by the user controls 212. For example, one or more parameter settings may determine, at least in part, a gain of one or more gain elements of the audio processing circuit 230. As another example, one or more parameter settings may determine, at least in part, a frequency response of one or more filters that operate on audio signals in the audio processing circuit 230. As another example, one or more parameter settings may determine, at least in part, whether and which sound effects are added to audio signals in the audio processing circuit 230 (e.g., which effects to add to microphone audio to morph the user's voice). Example parameter settings which affect audio processing are described in the co-pending U.S. patent application Ser. No. 13/040,144 titled "Gaming Headset with Programmable Audio" and published as US2012/0014553, the entirety of which is hereby incorporated herein by reference. Particular parameter settings may be selected autonomously by the headset 200 in accordance with one or more algorithms, based on user input (e.g., via controls 212), and/or based on input received via one or more of the connectors 210 and 214.

The storage device 224 may also be operable to store audio information such as the determined number of audio channels for a particular audio source and/or particular audio type. The audio information may be stored as, for example, a look up table (LUT) in the storage device 224.

In another embodiment of the disclosure, the CPU 222 may be operable to configure the audio processing circuit 230 to perform signal analysis on the audio signal(s) received via the connector 210 and/or the radio 220. The signal analysis may be utilized to determine the type of input stream that is being received by the headset 200. The CPU 222 may be operable to control the operation of the audio processing circuit 230 in order to store (e.g., in the storage device 224) the results of the audio analysis for different received signals along with an identifier (e.g., a name and/or signature of the particular content and/or source device from which content is being received) of the received signals that may be used in quickly determining characteristics of future signals rather than having to re-perform signal analysis.

The memory 226 may comprise suitable logic, circuitry, interfaces and/or code that may comprise volatile memory used by the CPU 222 and/or audio processing circuit 230 as program memory, for storing runtime data, etc. In this regard, the memory 226 may comprise information and/or data that may be utilized to control operation of the audio processing circuit 230 to determine characteristics of the audio signal(s) being received.

The audio processing circuit 230 may comprise suitable logic, circuitry, interfaces and/or code that may be operable to perform audio processing functions such as volume/gain control, compression, decompression, encoding, decoding, introduction of audio effects (e.g., echo, phasing, virtual surround effect, etc.), and/or the like. As described above, the processing performed by the audio processing circuit 230 may be determined, at least in part, by which parameter settings have been selected. The processing performed by the audio processing circuit 230 may also be determined based on default settings, player preference, and/or by adaptive and/or dynamic changes to the game play environment. The processing may be performed on game, chat, and/or microphone audio that is subsequently output to speaker 216*a* and 216*b*. Additionally, or alternatively, the processing may be performed on chat audio that is subsequently output to the connector 210 and/or radio 220.

The audio processing circuit 230 may be operable to perform signal analysis on a received audio signal. The signal analysis may determine characteristics of the audio signal such as the number of audio channels present in the signal. The audio processing circuit 230 and the CPU 222 may be operable to control the volume of the channel(s) such that the resulting stereo output is bounded and does not fluctuate beyond certain levels regardless of the number of audio channels present in the audio signal. Additionally, based on the determined characteristics, the audio processing circuit 230 and the CPU 222 may be operable to process the channel(s) to create a desired surround or virtual effect such as controlling the perceived location of the listener relative to sources of sounds in the audio signal.

Figure 3A:
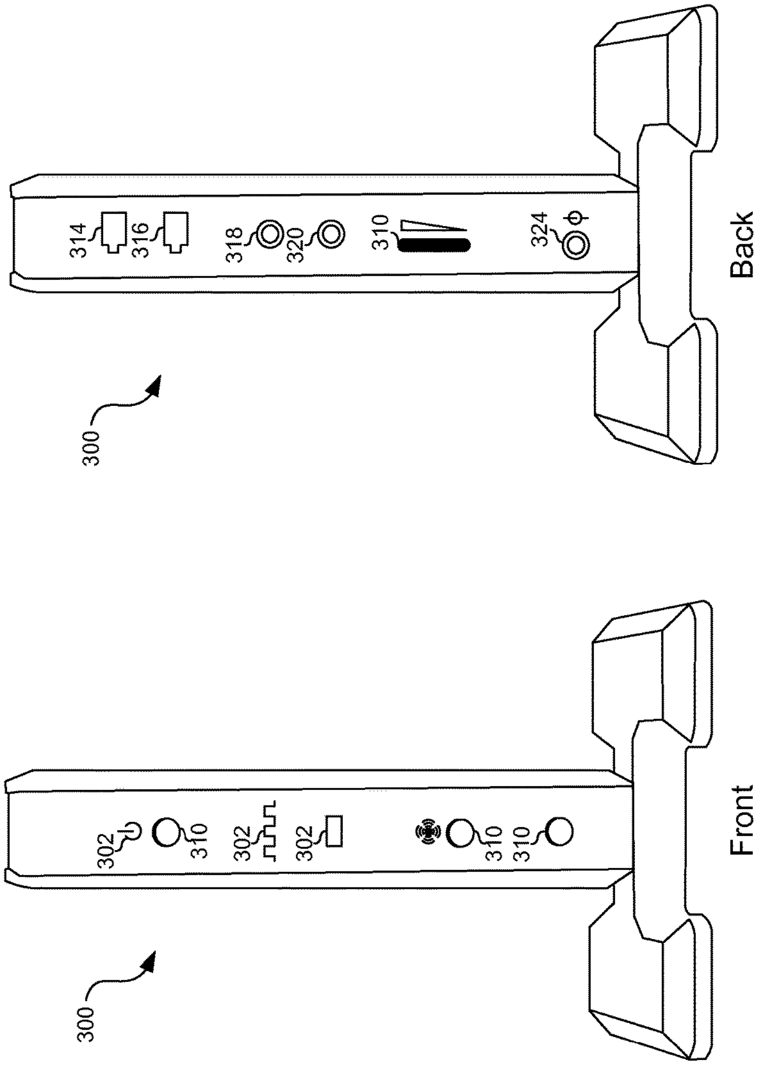
FIG. 3A is a diagram that depicts two views of an example embodiment of an audio basestation, in accordance with various exemplary embodiments of the disclosure.

FIG. 3A is a diagram that depicts two views of an example embodiment of an audio basestation, in accordance with various exemplary embodiments of the disclosure. Referring to FIG. 3A, there is shown an exemplary embodiment of an audio basestation 301. The basestation 301 comprises status indicators 302, user controls 310, power port 324, and audio connectors 314, 316, 318, and 320.

The audio connectors 314 and 316 may comprise digital audio in and digital audio out (e.g., S/PDIF) connectors, respectively. The audio connectors 318 and 320 may comprise a left “line in” and a right “line in” connector, respectively. The controls 310 may comprise, for example, a power button, a button for enabling/disabling virtual surround sound, a button for adjusting the perceived angles of the speakers when the virtual surround sound is enabled, and a dial for controlling a volume/gain of the audio received via the “line in” connectors 318 and 320. The status indicators 302 may indicate, for example, whether the audio basestation 301 is powered on, whether audio data is being received by the basestation 301 via connectors 314, and/or what type of audio data (e.g., Dolby Digital) is being received by the basestation 301.

Figure 3B:
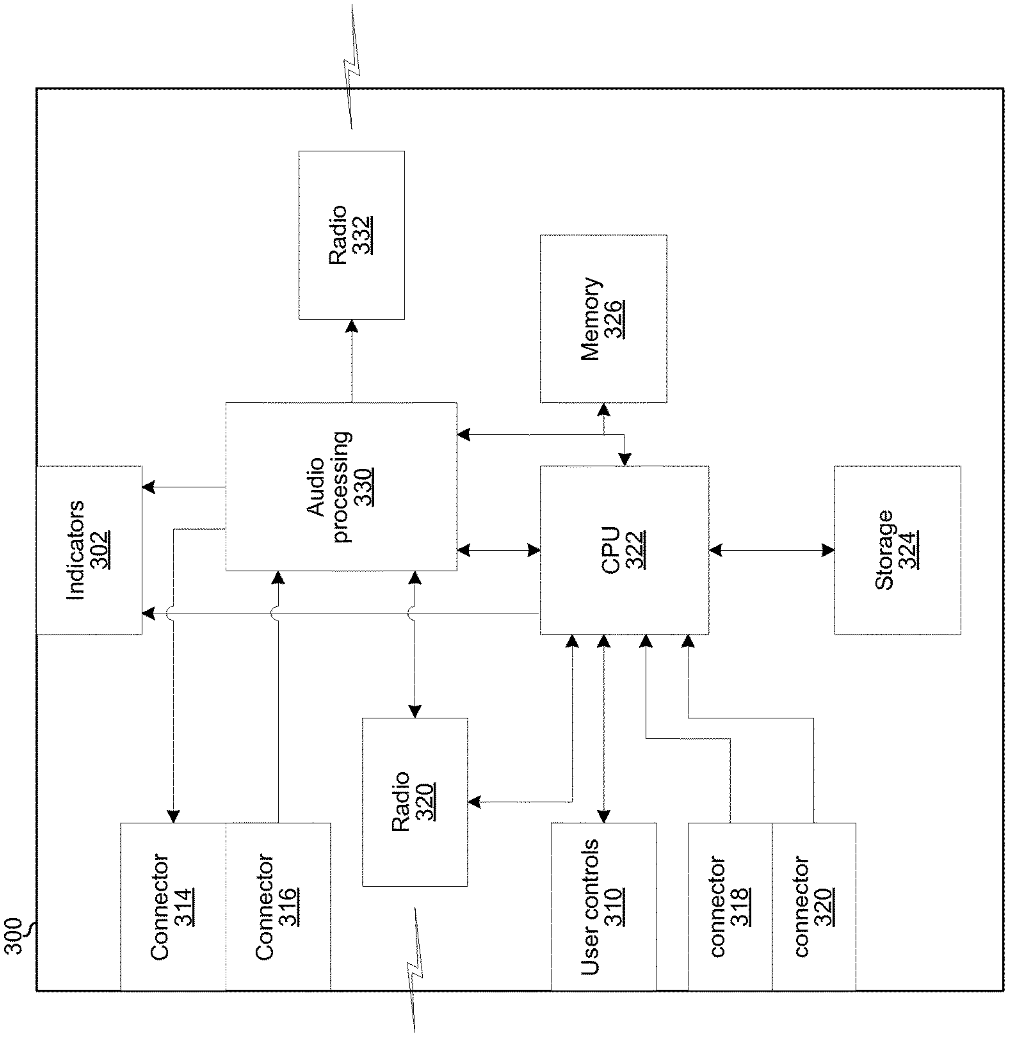
FIG. 3B is a diagram that depicts a block diagram of the audio basestation, in accordance with various exemplary embodiments of the disclosure.

FIG. 3B is a diagram that depicts a block diagram of the audio basestation 301, in accordance with various exemplary embodiments of the disclosure. Referring to FIG. 3B, there is shown an exemplary embodiment of an audio basestation 301. In addition to the user controls 310, indicators 302, and connectors 314, 316, 318, and 320 described above, the block diagram additionally shows a CPU 322, a storage device 324, a memory 326, a radio 320, an audio processing circuit 330, and a radio 332.

The radio 320 comprises suitable logic, circuitry, interfaces and/or code that may be operable to communicate in accordance with one or more standardized (such as the IEEE 802.11 family of standards, the Bluetooth family of standards, NFC, and/or the like) and/or proprietary (e.g., proprietary protocol for receiving audio protocols for receiving audio from a console such as the console 176) wireless protocols.

The radio 332 comprises suitable logic, circuitry, interfaces and/or code that may be operable to communicate in accordance with one or more standardized (such as, for example, the IEEE 802.11 family of standards, the Bluetooth family of standards, and/or the like) and/or proprietary wireless protocol(s) (e.g., a proprietary protocol for transmitting audio to the headphones 200).

The CPU 322 comprises suitable logic, circuitry, interfaces and/or code that may be operable to execute instructions for controlling/coordinating the overall operation of the audio basestation 301. Such instructions may be part of an operating system or state machine of the audio basestation 301 and/or part of one or more software applications running on the audio basestation 301. In some implementations, the CPU 322 may be, for example, a programmable interrupt controller, a state machine, or the like.

The storage 324 may comprise, for example, FLASH or other nonvolatile memory for storing data which may be used by the CPU 322 and/or the audio processing circuit 330. Such data may include, for example, parameter settings that affect processing of audio signals in the basestation 301. For example, one or more parameter settings may determine, at least in part, a gain of one or more gain elements of the audio processing circuit 330. As another example, one or more parameter settings may determine, at least in part, a frequency response of one or more filters that operate on audio signals in the audio processing circuit 330. As another example, one or more parameter settings may determine, at least in part, whether and which sound effects are added to audio signals in the audio processing circuit 330 (e.g., which effects to add to microphone audio to morph the user’s voice). Example parameter settings which affect audio processing are described in the co-pending U.S. patent application Ser. No. 13/040,144 titled “Gaming Headset with Programmable Audio” and published as US2012/0014553, the entirety of which is hereby incorporated herein by reference. Particular parameter settings may be selected autonomously by the basestation 301 in accordance with one or more algorithms, based on user input (e.g., via controls 310), and/or based on input received via one or more of the connectors 314, 316, 318, and 320.

The memory 326 may comprise volatile memory used by the CPU 322 and/or audio processing circuit 330 as program memory, for storing runtime data, etc.

The audio processing circuit 330 may comprise suitable logic, circuitry, interfaces and/or code that may be operable to perform audio processing functions such as volume/gain control, compression, decompression, encoding, decoding, introduction of audio effects (e.g., echo, phasing, virtual surround effect, etc.), and/or the like. As described above, the processing performed by the audio processing circuit 330 may be determined, at least in part, by which parameter settings have been selected. The processing may be performed on game and/or chat audio signals that are subsequently output to a device (e.g., headset 200) in communication with the basestation 301. Additionally, or alternatively, the processing may be performed on a microphone audio signal that is subsequently output to a device (e.g., console 176) in communication with the basestation 301.

Figure 4:
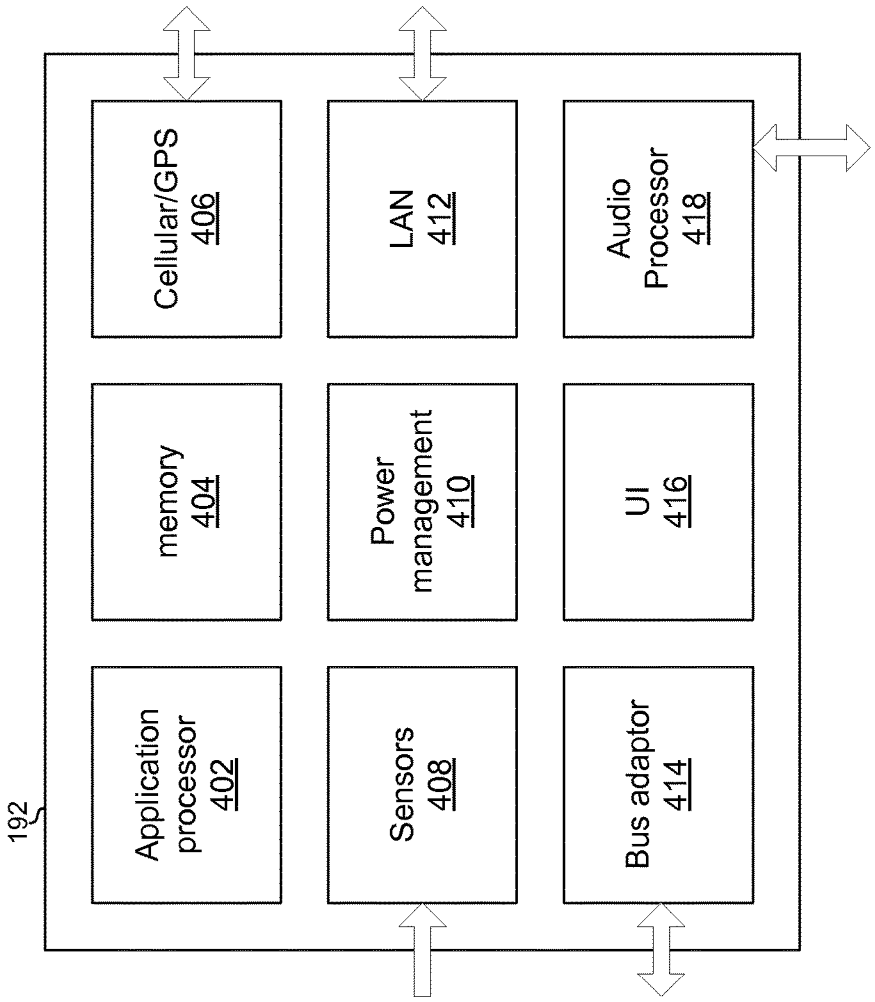
FIG. 4 is a block diagram of an exemplary multi-purpose device, in accordance with various exemplary embodiments of the disclosure.

FIG. 4 is a block diagram of an exemplary multi-purpose device 192, in accordance with various exemplary embodiments of the disclosure. The example multi-purpose device 192 comprises an application processor 402, memory subsystem 404, a cellular/GPS networking subsystem 406, sensors 408, power management subsystem 410, LAN subsystem 412, bus adaptor 414, user interface subsystem 416, and audio processor 418.

The application processor 402 comprises suitable logic, circuitry, interfaces and/or code that may be operable to execute instructions for controlling/coordinating the overall operation of the multi-purpose device 192 as well as graphics processing functions of the multi-purpose device 1922. Such instructions may be part of an operating system of the console and/or part of one or more software applications running on the console.

The memory subsystem 404 comprises volatile memory for storing runtime data, nonvolatile memory for mass storage and long-term storage, and/or a memory controller which controls reads/writes to memory.

The cellular/GPS networking subsystem 406 comprises suitable logic, circuitry, interfaces and/or code that may be operable to perform baseband processing and analog/RF processing for transmission and reception of cellular and GPS signals.

The sensors 408 comprise, for example, a camera, a gyroscope, an accelerometer, a biometric sensor, and/or the like.

The power management subsystem 410 comprises suitable logic, circuitry, interfaces and/or code that may be operable to manage distribution of power among the various components of the multi-purpose device 192.

The LAN subsystem 412 comprises suitable logic, circuitry, interfaces and/or code that may be operable to perform baseband processing and analog/RF processing for transmission and reception of cellular and GPS signals.

The bus adaptor 414 comprises suitable logic, circuitry, interfaces and/or code that may be operable for interfacing one or more internal data busses of the multi-purpose device with an external bus (e.g., a Universal Serial Bus) for transferring data to/from the multi-purpose device via a wired connection.

The user interface subsystem 416 comprises suitable logic, circuitry, interfaces and/or code that may be operable to control and relay signals to/from a touchscreen, hard buttons, and/or other input devices of the multi-purpose device 192.

The audio processor 418 comprises suitable logic, circuitry, interfaces and/or code that may be operable to process (e.g., digital-to-analog conversion, analog-to-digital conversion, compression, decompression, encryption, decryption, resampling, etc.) audio signals. The audio processor 418 may be operable to receive and/or output signals via a connector such as a 3.5 mm stereo and microphone connector.

Figure 5:
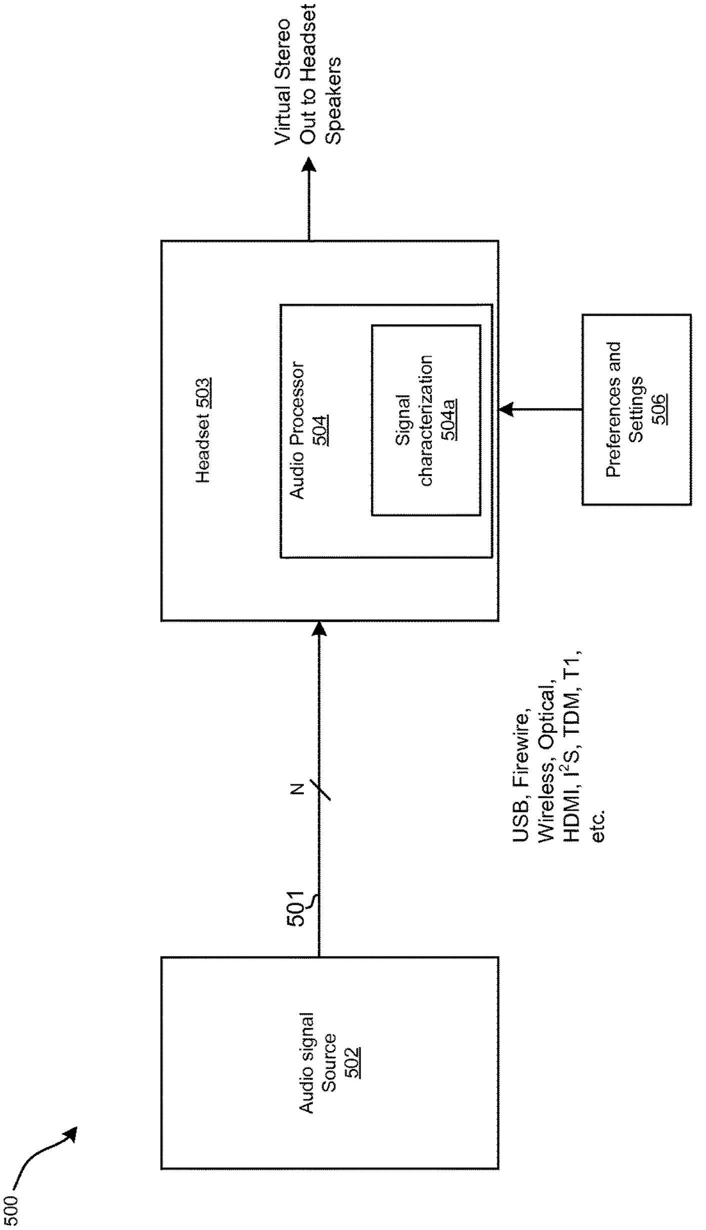
FIG. 5 is a block diagram of an exemplary processing subsystem in a headset, which may be utilized to determine characteristics of a received audio signal, in accordance with en exemplary embodiment of the disclosure.

FIG. 5 is a block diagram of an exemplary processing subsystem in a headset, which may be utilized to determine characteristics of a received audio signal, in accordance with en exemplary embodiment of the disclosure. Referring to FIG. 5, there is shown a processing subsystem 500 comprising audio source 502, a headset 503 and a preferences and setting module 506. The headset 503 may comprise an audio processor 504. The audio processor 504 comprises a signal characterization module 504*a*.

The headset 503 may be substantially similar to the headset 200, which is shown and described with respect to, for example, FIGS. 2A, 2B and 2C.

The audio source 502 may comprise suitable logic, circuitry, interfaces and/or code that may be operable to output one or more of a plurality of audio signals. Each of the audio signals that are output by the audio source 502 may comprise two or more audio channels, where N is an integer. For 7.1 surround, for example, N equals eight and the audio channels carried by signal(s) 501 may comprise, left front (LF), right front (RF), center (C), left side (LS), right side (RS), left rear (LR), right rear (RR), and sub-woofer. The signal(s) 501 from the audio source 502 may communicated to headset 503 via, for example, USB, Firewire, Wireless, Optical, HDMI, $I^2S$, TDM, T1, and so on.

The audio processor 504 may be substantially similar to the audio processing circuit 230, for example, which is shown and described with respect to, FIG. 2C.

The preferences and setting module 506 may comprise listener or player preference information and settings for different games, music, and/or movies. The information for the user preferences and settings module 506 may be stored, for example, in the storage device 224, which is shown and described with respect to, FIG. 2C.

The signal characterization module 504*a* in the audio processor 504 is operable to perform signal analysis on the audio signals that are received from the audio source 502 to determine type of audio signal (e.g., whether it is mono, stereo, 6 channel surround, or eight channel surround). The signal characterization module 504*a* may be operable to monitor, for a determined period of time, the audio levels on possible audio channels of the received signal 501. If no signal is detected on both the left channel and the right channel during the period of time, the signal characterization module 504*a* may conclude that there is no audio in the received signal 501. If, on the other hand, the signal characterization module 504*a* detects audio on only one of the left and right channels during the period of time, and the audio level (e.g., instantaneously, peak, RMS, time averaged, or any other suitable measure of level) during the period of time is above a first determined threshold, the signal characterization module 504*a* determines that the audio is monophonic (mono). If the signal characterization module 504*a* detects audio on both the left channel and the right channel and the detected audio level on each of the left channel and the right channel is above a second determined threshold, the signal characterization module 504*a* determines that the audio is at least stereo. If the signal characterization module 504*a* determines that the audio is at least stereo, the signal characterization module 504*a* checks the audio level(s) of the subwoofer channel and/or the center channel during the determined period of time. If the signal characterization module 504*a* determines that the audio level(s) on the subwoofer channel and/or center channel during the monitoring period are above a third determined threshold, the signal characterization module 504*a* may conclude that there are at least six channels present in the received audio signal 501.

In order to determine whether there are six channels or eight channels, in the signal(s) 501 output from the audio source 502, the signal characterization module 504*a* may check the audio level(s) on one or both of the side channels during the monitored period of time. If the signal characterization module 504*a* determines that the audio level(s) of one or both of the side channels are above a fourth threshold, the signal characterization module 504*a* determines that there are eight channels. If, on the other hand, the signal characterization module 504*a* determines that the audio level(s) of one or both of the side channels are not above the fourth threshold, the signal characterization module 504*a* determines that there are six channels.

The CPU 222 (FIG. 2C) and/or the audio processor 504 may be operable to utilize the decision as to the type of signal 501 for controlling the volume of the detected channel(s) such that the resulting stereo output does not fluctuate beyond certain levels regardless of the number of channels carried in the signal(s) 501. The CPU 222 (FIG. 2C) and/or the audio processor 504 may also be operable to utilize the information about the signal 501 that is stored by the signal characterization module 504*a* in the storage device 324 to process the signal 501 for creating a desired surround effect, for example, by controlling the perceived location of the listener relative to sound sources in the audio.

Figure 6:
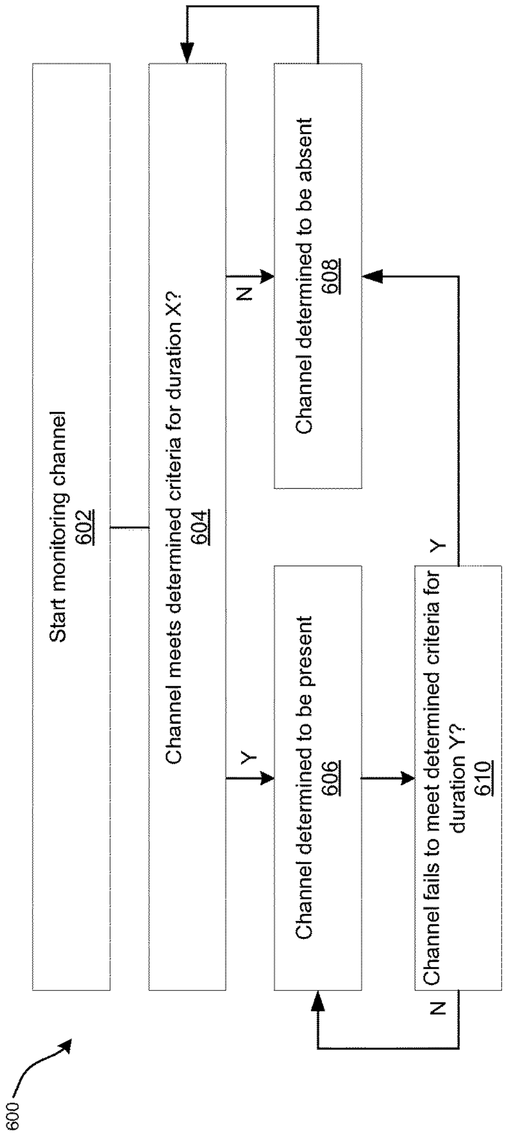
FIG. 6 is a flow diagram illustrating exemplary steps for signal characterization, in accordance with various exemplary embodiments of the disclosure.

FIG. 6 is a flow diagram illustrating exemplary steps for signal characterization, in accordance with various exemplary embodiments of the disclosure. In block 502, the signal characterization circuit 504*a* begins monitoring a channel of received signal 501 (e.g., any one of the 8 channels of a 7.1 Surround signal).

In block 604, the signal characterization circuit 504*a* determines whether the monitored signal meets determined criteria for a determined period of time X. The criteria may be, for example, whether the level of the channel is above a threshold for the entire period of time X, for some percentage of the period of time X, or the like. The criteria may be set based, for example, on the type of channel being monitored (e.g., which of the eight channels it is) and/or on the type of device that the audio source 502 is. For example, if the audio source 502 is a game console, or television, or blue-ray player the criteria may be set with a bias toward deciding that the audio signal is a surround sound signal, since those types of devices typically output surround sound signals. Setting the criteria to have such a bias may comprise, for example, using a lower threshold for deciding that a surround channel is present (e.g., subwoofer, center, left side, and/or right side) before deciding that the signal 501 is a surround signal. As another example, if the audio source 502 is a stereo or personal audio device, the criteria may be set with a bias toward deciding that the signal is a stereo signal since those types of devices typically output stereo signals. Setting the criteria to have such a bias may comprise, for example, using a higher level threshold for deciding that a surround channel is present (e.g., subwoofer, center, left side, and/or right side) before deciding that the signal 501 is a surround signal. Similarly, the value of X may be set based on the type of audio device and/or the type of channel. For example, X may be longer for channels, such as the rear channels of a surround signal, that have sound on them relatively infrequently and shorter for channels, such as center, that have sound on them relatively frequently.

Still referring to block 604, if the channel meets the criteria for the determined amount of time X, the process advances to block 606 and the channel is decided to be present. If the channel does not meet the criteria for the determined amount of time X, the process advances to block 608 and the channel is decided to be absent.

In block 606, the monitored channel is determined to be present and volume control settings are set accordingly. After block 606, the process advances to block 610.

In block 608, the monitored channel is determined to be absent and volume control settings are set accordingly.

In block 610, it is determined whether the channel has failed to meet the criteria for a period of time Y (where Y may be different than X). If so, then the process advances to block 608. If not, the process returns to block 606. The value of Y may be set based on the type of audio device and/or the type of channel. For example, Y may be longer for channels, such as the rear channels of a surround signal, that have sound on them relatively infrequently and shorter for channels, such as center, that have sound on them relatively frequently.

As another example to illustrate setting X and Y, for a surround channel (e.g., subwoofer and/or center) from an audio source 502 that typically outputs surround audio (e.g., a game console), X may be shorter than Y, thus creating a bias for deciding that the signal is surround and remaining in surround mode until it there is high confidence that the audio is no longer surround.

As utilized herein the terms "circuits" and "circuitry" refer to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Throughout this disclosure, the use of the terms dynamically and/or adaptively with respect to an operation means that, for example, parameters for, configurations for and/or execution of the operation may be configured or reconfigured during run-time (e.g., in, or near, real-time) based on newly received or updated information or data. For example, an operation within a transmitter and/or a receiver may be configured or reconfigured based on, for example, current, recently received and/or updated signals, information and/or data.

The present method and/or system may be realized in hardware, software, or a combination of hardware and software. The present methods and/or systems may be realized in a centralized fashion in at least one computing system, or in a distributed fashion where different elements are spread across several interconnected computing systems. Any kind of computing system or other apparatus adapted for carrying out the methods described herein is suited. A typical combination of hardware and software may be a general-purpose computing system with a program or other code that, when being loaded and executed, controls the computing system such that it carries out the methods described herein. Another typical implementation may comprise an application specific integrated circuit or chip. Some implementations may comprise a non-transitory machine-readable (e.g., computer readable) medium (e.g., FLASH drive, optical disk, magnetic storage disk, or the like) having stored thereon one or more lines of code executable by a machine, thereby causing the machine to perform processes as described herein.

While the present method and/or system has been described with reference to certain implementations, it will be understood by those skilled in the art that various changes may be made and equivalents may be substituted without departing from the scope of the present method and/or system. In addition, many modifications may be made to adapt a particular situation or material to the teachings of the present disclosure without departing from its scope. Therefore, it is intended that the present method and/or system not be limited to the particular implementations disclosed, but that the present method and/or system will include all implementations falling within the scope of the appended claims.

What is claimed is:

1. A method, comprising:

in an audio headset:

receiving one or more audio signals carrying audio channels; and processing said audio channels to generate stereo signals for output to a left and a right speaker of said audio headset, wherein said processing comprises:

determining a quantity of said audio channels carried in said one or more received audio signals by comparing a level of at least one channel of said one or more received audio signals to a threshold during a determined time period;

adjusting a signal level of one or more of said audio channels based on said determined quantity of said audio channels carried in said one or more received audio signals such that a lower determined quantity of audio channels allows a higher signal level per channel as compared to a higher determined quantity of audio channels; and combining said audio channels to generate said stereo signals.

2. The method of claim 1, wherein said processing comprises adjusting gain and/or phase of said audio channels carried in said one or more received audio signals such that a perceived location of a listener wearing said headset relative to a source of sounds carried in said one or more received audio signals is changed.

3. The method of claim 1, wherein said determining said quantity of said audio channels comprises:

determining a level of audio on a left channel of said one or more received audio signals during said determined time period; and determining a level of audio on a right channel of said one or more received audio signals during said determined time period.

4. The method of claim 3, wherein said quantity of said audio channels is determined to be one audio channel when only one of said level of said audio on said left channel and said level of said audio on said right channel is above said threshold during said determined time period.

5. The method of claim 4, wherein said quantity of said audio channels is determined to be at least two audio channels when said level of said audio on said left channel is above said threshold during said determined time period and said level of said audio on said right channel is above said threshold during said determined time period.

6. The method of claim 1, wherein said quantity of said audio channels is determined to be eight audio channels when a level of audio on one or more side channels of said one or more received audio signals is above said threshold during said determined time period.

7. The method of claim 6, wherein said quantity of said audio channels is determined to be six audio channels if said level of audio on said one or more side channels is below said threshold during said determined time period.

8. The method of claim 1, wherein said determining comprises:

determining a type of audio source from which said one or more received audio signals originated.

9. A system, comprising:

an audio headset, said audio headset comprising a signal characterization circuit operable to:

receive one or more audio signals carrying audio channels; and process said audio channels to generate stereo signals for output to a left and a right speaker of said audio headset, wherein said processing of said audio channel comprises:

determination of a quantity of said audio channels carried in said one or more received audio signals—by comparing a level of at least one channel of said one or more received audio signals to a threshold during a determined time period;

adjustment of a signal level of one or more of said audio channels based on said determined quantity of said audio channels carried in said one or more received audio signals such that a lower determined quantity of audio channels allows a higher signal level per channel as compared to a higher determined quantity of audio channels; and combining said audio channels to generate said stereo signals.

10. The system of claim 9, wherein said processing of said audio channels comprises adjustment of gain and/or phase of said audio channels carried in said one or more received audio signals such that a perceived location of a listener wearing said headset relative to a source of sounds carried in said one or more received audio signals is changed.

11. The system of claim 9, wherein said determination of said quantity of said audio channels comprises:

determination of a level of audio on a left channel of said one or more received audio signals during said determined time period; and determination of a level of audio on a right channel of said one or more received audio signals during said determined time period.

12. The system of claim 11, wherein said quantity of said audio channels is determined to be one audio channel when only one of said level of said audio on said left channel and said level of said audio on said right channel is above said threshold during said determined time period.

13. The system of claim 12, wherein said quantity of said audio channels is determined to be at least two when said level of said audio on said left channel is above said threshold during said determined time period and said level of said audio on said right channel is above said threshold during said determined time period.

14. The system of claim 9, wherein said quantity of said audio channels is determined to be to be eight audio channels when a level of audio on one or more side channels of said one or more received audio signals is above said threshold during said determined time period.

15. The system of claim 14, wherein said quantity of said audio channels is determined to be six audio channels if said level of audio on said one or more side channels is below said threshold during said determined time period.

16. The system of claim 9, wherein said determination comprises:

determination of a type of audio source from which said one or more received audio signals originated.

17. A non-transitory computer readable medium having stored thereon, a computer program having at least one code section that is executable by an audio headset for causing the audio headset to perform:

receiving one or more audio signals carrying audio channels; and processing said audio channels to generate stereo signals for output to a left and a right speaker of said audio headset, wherein said processing comprises:

determining a number of said audio channels carried in said one or more received audio signals by comparing a level of at least one channel of said one or more received audio signals to a threshold during a determined time period;

adjusting a signal level of one or more of said audio channels based on said determined number of said audio channels such that a lower determined quantity of audio channels allows a higher signal level per channel as compared to a higher determined quantity of audio channels; and combining said audio channels to generate said stereo signals.

18. The non-transitory computer readable medium of claim 17, wherein said determining said quantity of said audio channels comprises:

determining a level of audio on a left channel of said one or more received audio signals during said determined time period; and determining a level of audio on a right channel of said one or more received audio signals during said determined time period.

19. The non-transitory computer readable medium of claim 18, wherein said quantity of said audio channels is determined to be one audio channel when only one of said level of said audio on said left channel and said level of said audio on said right channel is above said threshold during said determined time period.

20. The non-transitory computer readable medium of claim 19, wherein said quantity of said audio channels is determined to be at least six audio channels when a level of audio on a subwoofer channel and/or on a center channel of said one or more received audio signals is above said threshold during said determined time period.

* * * * *